United States Patent [19]
Schlaefer

[11] 4,151,117
[45] Apr. 24, 1979

[54] NOVEL OXIDATION CATALYST AND PRODUCTION OF UNSATURATED ALDEHYDES, ACIDS AND NITRILES THEREWITH

[75] Inventor: Francis W. Schlaefer, Pennsauken, N.J.

[73] Assignee: Rohm and Haas Company, Philadelphia, Pa.

[21] Appl. No.: 490,449

[22] Filed: Jul. 22, 1974

Related U.S. Application Data

[63] Continuation of Ser. No. 178,507, Sep. 7, 1971, abandoned, which is a continuation-in-part of Ser. No. 149,343, Jun. 2, 1971, abandoned.

[51] Int. Cl.$^2$ .................. B01J 27/18; B01J 27/02
[52] U.S. Cl. .................. 252/437; 252/435; 252/439; 260/465.3; 260/604 R; 252/301.1 R; 562/546; 562/548
[58] Field of Search ............... 252/437–439, 252/435

[56] References Cited

U.S. PATENT DOCUMENTS

| | | | |
|---|---|---|---|
| 3,102,147 | 8/1963 | Johnson | 252/437 X |
| 3,226,421 | 12/1965 | Giordano et al. | 252/439 X |
| 3,254,110 | 5/1966 | Sennewald et al. | 252/437 X |
| 3,338,952 | 8/1967 | Callahan et al. | 252/439 X |
| 3,412,135 | 11/1968 | Eden | 252/437 X |
| 3,445,500 | 5/1969 | Eden | 252/437 X |
| 3,487,109 | 12/1969 | Kurata et al. | 252/439 X |
| 3,520,923 | 7/1970 | Eden | 252/437 X |
| 3,522,299 | 7/1970 | Takenaka et al. | 252/437 X |
| 3,527,716 | 9/1970 | Nemec et al. | 252/439 |
| 3,668,147 | 6/1972 | Yoshino et al. | 252/439 X |
| 3,703,550 | 11/1972 | Nakano et al. | 252/437 X |

*Primary Examiner*—Patrick Garvin
*Assistant Examiner*—Lillie Richards

[57] ABSTRACT

The present invention relates to the discovery of a new catalyst and in methods for the preparation of oxidation products such as unsaturated acids, nitriles, and aldehydes by vapor phase oxidation in the presence of the catalyst. The catalyst gives high productivity of desired products over a prolonged period of operation, high selectivity over a prolonged period of operation and prolonged life of the oxidation catalyst system.

The catalyst, on a molar basis, has the composition $Sb_{0-.1}Sn_{0-.1}Te_{.001-1}As_{0-1}A_{0-1}/Y_{12}X_{2-12}Sb_{0-1}Th_{.01-1}U_{0-2}Si_{0-50}P_{0-5}O_x$, wherein A is Bi and/or Cd, and X is Co or Fe or both, and Y is Mo or W, or both.

9 Claims, No Drawings

NOVEL OXIDATION CATALYST AND PRODUCTION OF UNSATURATED ALDEHYDES, ACIDS AND NITRILES THEREWITH

This is a continuation of application Ser. No. 178,507, filed Sept. 7, 1971 and now abandoned, which in turn was a continuation-in-part of application Ser. No. 149,343, filed June 2, 1971 and now also abandoned.

The invention relates to the preparation of unsaturated carboxylic acids and unsaturated aldehydes, or unsaturated nitriles, by the oxidation of the corresponding aldehyde or olefin. Methacrolein, in particular, is prepared by the oxidation of isobutylene. Methacrylic acid is also obtained in a minor proportion.

Many attempts and many catalyst systems have been employed by the art to achieve conversion of propylene to acrolein, acrylic acid and acetic acid and of isobutylene to methacrolein and methacrylic acid. The art indicates that conversion requires high temperatures and large volumes of gases. These conditions foster substantial costs in the construction and maintenance of reactors. Accordingly, for maximum commercial utility, it is imperative that productivity be maintained at a high level. Various degrees of success have been achieved by prior art systems by resorting to the use of high oxygen-propylene ratios, high reactor temperatures and various combinations of promoters and catalysts. The high ratios and temperatures favorably affect productivity per reactor volume but lead to increased waste gas formation. Also, promoters tend to be volatile and toxic, thereby requiring additional equipment for control and reuse. By and large, the known processes present the possibility and actual realization of increased waste gas formation, toxicity problems from the use of volatile promoters, expensive reactor construction and inefficient operation due to catalyst deterioration.

The patent literature abounds with statements to the effect that a given catalyst is useful for the preparation of aldehydes from unsaturated olefins, and implications are sometimes made that a given catalyst is equally efficacious for oxidizing propylene and for oxidizing isobutylene to give, respectively, acrolein and methacrolein. The applicants have found this is not the general rule. A catalyst or support which provides activity of a nature to convert propylene to acrolein, when utilized with isobutylene, results in excessive conversion of starting material to waste products such as carbon monoxide and carbon dioxide. Conversely, a catalyst useful for converting isobutylene to methacrolein results in a very low conversion of propylene to desired products. For example, when pyrogenic silica is utilized as a support for a catalyst containing cobalt molybdate or iron molybdate, it is excellent for converting propylene to acrolein, but results in excessive waste products when utilized with isobutylene at useful reaction temperatures.

The objects and advantages of the highly critical nature of the catalysts are as follows:

(1) High productivity over a prolonged period

High productivity should be maintained even after extended periods of operation. This stability of production is particularly important in commercial operations where decreases in the aldehydes and acid content of the product stream substantially reduce the efficiency of the equipment used to isolate the aldehydes and acids.

(2) High selectivity over a prolonged period

By employing the catalysts of the present invention, one can increase the aldehyde and acid productivity without being burdened by an increased rate of over-oxidation. This not only results in efficient use of the raw material, but also reduces the substantial heat load caused by the production of waste gas and saturated acids. This results in more efficient reactor utilization and also produces a higher concentration of desired aldehydes and acids in the reactor effluent. This enables the subsequent isolation of the aldehydes and acids to proceed with maximum efficiency.

(3) Prolonged physical stability and activity

In the field of catalysis, physical stability normally refers to the ability of a catalyst to withstand pressure and abrasion. Such are encountered in heterogeneous catalytic reactors and cause less stable catalysts to crumble into smaller particles or fines. The occurrence of the latter is particularly undesirable in that they restrict gas flow through the reactor. Ultimately, a point is reached where the pressure drop is appreciable and flow becomes nearly impossible. The catalyst must then be replaced. Loss of activity also requires catalyst replacement. Since commercial reactors normally contain a plurality of small diameter tubes, frequently several thousand or more, catalyst replacement is exceedingly time consuming. In addition to the lack of productivity during shutdown, one must also bear the economic burden of synthesizing and charging fresh catalyst more frequently.

The present invention comprises a process whereby oxygen and an olefin are continuously reacted to produce the corresponding unsaturated aldehyde and acid, or the nitrile, if ammonia is present. When ammonia is also present, the unsaturated nitrile is obtained.

Various prior art supports for catalysts for oxidizing propylene to acrolein or acrylonitrile or isobutylene to methacrolein or methacrylonitrile are useful, silica, silica diatomaceous earth, kieselguhr, silicon carbide, clay, aluminum oxides, carbon, pumice, alundum, titania, Carborundum, Alundum, colloidal silica, porcelain, bentonite, bauxite, silica gel, glass, fused quartz, coke, metallic aluminum, iron, copper, nickel, cobalt, or chromium, vermiculite, pyrogenic oxides of colloidal fineness prepared by oxidation of the halides of aluminum, zirconium, titanium, and silicon in the presence of steam at temperatures of about 1000° F., pozzoluana, dawsonite, montmorillonite, green sand, zeolites, permutites, activated carbon, crushed brick, magnesia, asbestos, and mineral wool, Of course, the perlite of said application, Ser. No. 149,343, is also useful.

The expanded, crushed perlite used according to the invention of Ser. No. 149,343 has certain critical characteristics as regards surface area, pore size, pore size distribution, and total porosity. For example, a silica catalyst support suitable for converting propylene to acrolein desirably which has a surface area in the neighborhood of 40 to 50 m.$^2$/g., is not wholly suitable for converting isobutylene to methacrolein. The perlite useful in accordance with the invention has the following properties:

| Properties | Useful Range | Preferred | Most Preferred |
|---|---|---|---|
| total surface area, m.$^2$/g. | <15 | <10 | <5 |
| total porosity, cc./g. | >2.5 | >2.8 | >3 |
| pore size distribution | | | |
| >100,000 Å (macropores) | >40% | >55% | >60% |
| 100,000 Å to 10,000 Å | | | |

| Properties | Useful Range | Preferred | Most Preferred |
|---|---|---|---|
| (medium size pores) 10,000 Å to 1,000 Å | | the balance | |
| (micropores) | <15% | <10% | <6% |
| <1,000 Å (micropores) | <10% | <5% | <4% |

The pore size distribution is expressed as a percentage of the total pore volume. Another desirable feature is the particle size of the perlite. It should pass through a 325 mesh screen, U.S. Sieve Series. Preferably, 75 to 100 percent passes through a 400 mesh screen. Silica has quite a different pore size distribution, having much fewer macropores (>100,000 Å), about the same medium range (the "balance" in table above), and much more in the microporous range of pore size (<10,000 Å). Silica is particularly useful as a support for propylene oxidation.

A support is to be distinguished from a diluent, i.e., the catalyst is formed in the presence of the support in the presence of a liquid, and then the mixture is dried and calcined so that the catalyst appears on the surface of the support and is not simply intermingled physically therewith. Regardless of the identity of the support, it should be tested first, with a given catalyst, before large scale work is conducted.

The novel catalyst is $Sb_{0-.1}Sn_{0-.1}Te_{.001-.1}As_{0-.1}A_{0-.1}/Y_{12}X_{2-12}Sb_{0-.1}Th_{.01-.1}U_{0-.2}Si_{0-.50}P_{0-.5}Ox$, on a molar basis, wherein A is Bi and/or Cd, and X is Co or Fe, and Y is Mo or W. The slash mark (/) dividing the left-hand portion and right-hand portion indicates that the materials on the left portion are added as promoters and in the form of water-insoluble compounds such as the tellurides. The materials on the right-hand portion are usually added as water-soluble compounds, it being understood that the materials are present in the final catalyst as the oxides resulting from calcining at a high temperature in the presence of air. The symbol "Ox" indicates that oxygen is combined with the elements to the extent necessary and inherent in the calcination process. Alternatively, without regard to the way the catalyst is made and the solubility of the starting materials, and on the basis solely of the elements in the finished catalyst, the composition can be stated as $Sb_{0-1.1}Sn_{0-.1}Te_{.001-.1}As_{0-.1}A_{0-.1}Y_{12}X_{2-12}Th_{.01-.1}U_{0-.2}Si_{0-.50}P_{0-.5}Ox$. This is identical to the preceding statement of composition, but without inclusion of the slash mark.

A particularly useful class of catalysts is represented by the following: $Sb_{.0001-.1}Sn_{.0001-.1}Te_{.001-.1}As_{0-.1}-A_{0-.1}/Mo_{12}Fe_{2-12}Sb_{.05-.1}Th_{.01-.1}U_{0-.2}Si_{0-.50}P_{0.001-.5}Ox$, with A having the same meaning as above, if the slash mark is omitted, the identically same catalyst, without regard to solubility of starting materials, is $Sb_{.0001-1.1}Sn_{.0001-.1}Te_{.001-.1}As_{0-.1}A_{0-.1}Mo_{12}Fe_{2-12}Th_{.01-.1}U_{0-.2}Si_{0-.50}P_{0.001-.5}Ox$.

To prepare the catalyst, an aqueous solution is prepared by dissolving salts of the catalsyt ingredients in deionized water and containing the support. The resulting solution is agitated while aqueous ammonia is added. After agitating for a short time, the promoters are added and the slurry is stripped, dried and then formed into pellets. If X is Co and Y is Mo, the slurry is filtered and stored in deionized water for 72 hours, and after filtering the filter cake is reslurried with deionized water and filtered again. The filter cake is calcined at 400° C. to 700° C. in the presence of an air stream.

The catalyst system when employed in the oxidative preparation of methacrolein and methacrylic acid by the reaction of isobutylene, oxygen and water, requires a temperature range of about 350° C. to about 500° C., preferably from 350° C. to about 460° C. For oxidizing propylene to acrolein and acrylic acid, the temperature is from about 300° C. to 500° C., preferably about 400° C. to 460° C.

For producing the nitriles, the temperature should be between 260° C. and 550° C., preferably 370° C. to 500° C. Isobutylene should be ammoxidized at a lower temperature than propylene. The ratio of ammonia, if any, to olefin is between about 0.05:1 and 5:1, on a molar basis.

Atmospheric pressure or pressures somewhat above atmospheric, such as about 1 to about 40 atmospheres, may be used. Usually atmospheric pressure is employed.

Oxygen may be used as such in the reaction or may be supplied as air. It is desirable in this reaction to employ a diluent to facilitate control of this highly exothermic reaction. Therefore, if oxygen is employed as such, it is preferred to employ a gaseous diluent, such as carbon dioxide, nitrogen or the like. The carbon dioxide diluent is most economically provided from the carbon dioxide produced in the process. If oxygen is employed as the normal approximately 20 percent component of air, then nitrogen is already present as a useful diluent. Generally, the use of oxygen as a component of air is quite satisfactory for the purpose of this reaction.

The olefin is employed in a ratio with respect to oxygen of 1:0.2 to 1:5, preferably 1:2.0 to 1:3.0.

The ratio of water to olefin is about 0.5:1 to 12:1, preferably about 3:1 to 8:1. The contact time can range from 20 seconds to as low as 0.1 second, but about 0.5 to about 5 seconds is preferred. Longer contact times generally produce higher conversions, but this is accompanied by an increase in waste gas formation. One skilled in the art may balance these two factors to obtain the contact time which results in the most economical operations.

The oxygen level in the feed is such as to result in an effluent from the reactor which contains at least 1.5 percent of oxygen. The upper level of oxygen, as a practical matter, is such that about 20 percent of oxygen is used in the feed. As to olefin in the feed, it ranges from about 5 percent to an absolute maximum of 20 percent. Water vapor in the feed as a practical minimum is 15 percent and may range up to about 60 percent; its absence creates problems.

To assist those skilled in the art to practice the present invention, the following modes of operation are suggested by way of illustration, ratios and percentages being by weight and the temperatures in °C. unless otherwise specifically noted. Exceptions are the catalyst, which is expressed in terms of atomic or mole ratios, and the vaporized reactants which are in volume precents (the same values also indicating mole percents).

EXAMPLE 1

A catalyst conforming to the formula

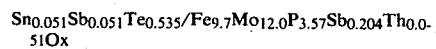

$Sn_{0.051}Sb_{0.051}Te_{0.535}/Fe_{9.7}Mo_{12.0}P_{3.57}Sb_{0.204}Th_{0.051}Ox$ is prepared as follows:

A 2 l. resin flask is charged with 90.8 g. phosphomolybdic acid ($20MoO_3 \cdot 2H_3PO_4 \cdot 48H_2O$), 154 g. ferric nitrate (Fe(NO$_3$)$_3$·9H$_2$O), 10.4 g. 87 percent phosphoric acid, 1.0 g. thorium nitrate (Th(NO$_3$)$_4$·4H$_2$O), 40 ml. 71 percent nitric acid, 890 ml. deionized water and 95 g. perlite having a surface area of <5 m.$^2$/g., a total porosity of about 2.8 cc./g. over 60 percent macropores, and less than about 7 percent micropores, 100 percent of which passes a 325 mesh sieve. The contents are then stirred at 60° to 65° while 342 g. of a 15 percent ammonia solution is added dropwise over a period of 35 minutes. Agitation of the thick slurry is continued while 2.5 g. antimony telluride (Sb$_2$Te$_3$), 1.5 g. molybdenum ditelluride (MoTe$_2$), 0.5 g. tin antimonide (SnSb) and 26 g. of the same perlite is added. The temperature is then raised and, while agitating, water is stripped off until a thick paste is obtained. The latter is formed into 3/16"×3/16" pellets and calcined in an air stream for 8 hours at 400° C. A 1"×32" tubular reactor, equipped with a preheater is charged with a mixture of 55.2 g. of the above and 113 ml. of nickel helices and then heated in a molten salt bath at 406° C. A feedstream containing 4.7 percent isobutylene, 13 percent oxygen, and 36 percent steam, nitrogen forming the balance. A high yield of methacrolein is obtained. Small amounts of methacrylic acid, acetone, acetaldehyde, formaldehyde, 2,3-butanedione, carbon monoxide, and carbon dioxide are also obtained.

When the same catalyst is used for oxidizing propylene to acrolein, using a temperature of about 470° C., a moderate yield of acrolein is obtained.

When this catalyst on perlite is calcined at 600° C., similar results are obtained except that it is virtually ineffective for propylene oxidation, giving only a very small yield of the more useful products.

EXAMPLE 2

A catalyst prepared similarly with a perlite support but having the formula $Sn_{0.0376}Sb_{0.0376}Te_{0.451}/Fe_{7.1-3}Mo_{12.0}P_{3.59}Sb_{0.15}Th_{0.0376}O_x$ gives similar results.

EXAMPLE 3

A catalyst conforming to the formula $Bi_{0.0578}Sn_{0.136}Sb_{0.136}Te_{1.64}/Fe_{7.1}Mo_{12.0}Si_{20.4}P_{2.54}Sb_{0.136}Th_{0.0327}O_x$ is prepared as follows:

A 2 l. resin flask equipped with a stirrer is charged with 95 g. colloidal silica, 181.6 g. phosphomolybdic acid, 21 g. 87 percent phosphoric acid, 308 g. ferric nitrate, 2.0 g. thorium nitrate, 694 ml. water and 56 ml. 71 percent nitric acid. The mixture is stirred at 60° to 65° while 509 g. of 14 percent aqueous ammonia solution is added over 40 minutes. Stirring is continued while 5.0 g. antimony telluride, 3.0 g. molybdenum ditelluride, 1.0 g. tin antimonide and 26 g. of colloidal silica are added. The stirred slurry is then converted to a thick paste by boiling off the excess water. The paste is bulk calcined for 8 hours in air at 612° to 635° C. This is ground to 60+ mesh and 115.5 g. charged to a 2 l. resin flask along with 0.77 g. tin antimonide, 7.12 g. molybdenum ditelluride, 0.85 g. bismuth telluride (Bi$_2$Te$_3$), 4.08 g. colloidal silica and 180 ml. deionized water. The slurry is heated, with stirring, to produce a loose paste. The latter is then used to coat 151 g. of silicon carbide previously impregnated with 5 w/w percent molybdenum trioxide. The granules are dried and then calcined for 8 hours at 426° to 442°. The yield of acrolein from propylene using conventional vapor phase oxidation conditions was about 37 percent, whereas isobutylene similarly oxidized gives a yield of 25 percent methacrolein, with 38 percent conversion of isobutylene to products. This shows that non-perlite supports are less effective in isobutylene oxidation.

EXAMPLE 4

Similar results to Example 3 are obtained using similarly prepared catalysts of the formulas $Sn_{0.051}Sb_{0.051}Te_{0.612}/Fe_{4.85}Mo_{12.0}Si_{0.56}P_{3.57}Sb_{0.204}Th_{0.051}O_x$ and $Sn_{0.0522}Sb_{0.0652}Te_{0.807}/Fe_{8.6}Mo_{12.0}Si_{8.52}P_{1.05}Th_{0.0391}Sb_{0.195}O_x$ supported, respectively, on colloidal silica and on Alundum. The first is a moderately good catalyst for oxidizing isobutylene to methacrolein but ineffective for propylene oxidation, contrary to the usual behavior of catalysts on silica supports, when oxidizing isobutylene, for reasons unknown. Perlite as a support far outperforms silica for oxidizing isobutylene. The second catalyst gives moderate yields of both aldehydes when starting with propylene and isobutylene.

EXAMPLE 5

A perlite-supported catalyst of the composition $Sn_{0.05}Sb_{0.08}Te_{0.52}/Fe_{9.85}Mo_{12.0}P_{3.56}Sb_{0.26}Th_{0.05}O_x$ is prepared as follows:

A 2 l. resin flask is charged with 90.8 g. phosphomolybdic acid (20MoO$_3$·2H$_3$PO$_4$·48H$_2$O), 154 g. ferric nitrate [Fe(NO$_3$)$_3$·9H$_2$O], 10.4 g. 87 percent phosphoric acid (H$_3$PO$_4$), 1.0 g. thorium nitrate (Th(NO$_3$)$_4$·4H$_2$O), 40 ml. 70 percent nitric acid, 888 ml. deionized water and 95 g. perlite. The contents are then stirred at 60° to 65°, while 308 g. of a 15 percent ammonia solution is added dropwise over a period of 40 minutes. Agitation of the thick slurry is continued while 3.1 g. antimony telluride (Sb$_2$Te$_3$), 1.5 g. molybdenum ditelluride (MoTe$_2$), 0.5 g. tin antimonide (SnSb) and 26 g. perlite are added. The temperatue is raised and, while agitating, the water is stripped off until a thick paste is obtained. The latter is formed into 3/16"×3/16" pellets, dried and calcined in an air stream for 8 hours at 511° C.

A 1"×32" tubular reactor, equipped with a preheater is charged with a mixture of 55.2 g. of the above and 113 ml. of nickel helices and then heated in a molten salt bath at 360° C. while a feedstream containing 4.7 percent isobutylene, 13.1 percent oxygen, 36.4 percent water and the balance nitrogen is passed over the bed. This results in a reactor temperature of 372° C. Product distribution data are shown in Table I. Subsequent to this test the bath is raised to 398° C. and another run made at a reactor temperature of 425°. Feeds are similar to those used in the preceding test. Data are shown in Table I.

EXAMPLE 6

A silica-supported catalyst of the following composition $Sn_{0.05}Sb_{0.07}Te_{0.52}/Fe_{9.85}Mo_{12.0}P_{3.56}Sb_{0.19}Th_{0.05}O_x/SiO_2$ is prepared.

Synthesis of this composition is generally similar to that used in Example 5. However, the calcining temperature is raised to 625° C. in an attempt to reduce the surface area in order to minimize the over-oxidations (relative to perlite) encountered when this type of support is used in oxidation of the sensitive $C_4$ hydrocarbons. The oxidation test is conducted at a reactor temperature of 370° C. and the data are shown in Table I. The silica is an amorphous colloidal pyrogenic silica commonly used for a support for vapor phase oxidation catalysts.

The data in Table I clearly indicate the superiority of the perlite support. Thus, at the 372° test, the perlite support results in much higher conversions to the desired product, methacrolein. This, moreover, is accomplished at the expense of over-oxidation to waste gas.

The finished catalyst material with a perlite support has about 90 percent of its pores of greater than 10,000 Å in size, the bulk falling in the range of 10,000 Å to 100,000 Å. The silica supported catalyst has about 90 percent of its pores in sizes below 10,000 Å, the bulk being in the 1,000 Å to 10,000 Å range. The original perlite support as such has a surface area of 1.8 m.²/g., about 65 percent of the pores being greater than 100,000 Å in size, about 30 percent between 10,000 Å and 100,000 Å, and only about 5 percent below 10,000 Å.

Table I

| | Comparison of Perlite with Silica | | | | | |
|---|---|---|---|---|---|---|
| | Reactor | Conv. | Percent Conversion to[3] | | | |
| Example | Temp. (° C.) | of $C_4H_8(\%)$[4] | MAcr[1] | MAA | HAc | Waste Gas |
| 5 (perlite support) | 372 | 44 | 29.9 | 0.6 | 1.7 | 5.5 |
| | 425 | 97 | 72.5 | 1.5 | 1.6 | 17.4 |
| 6 (SiO₂ support) | 370 | 33 | 10.7 | 0.3 | 0.9 | 14.3 |
| | 425[2] | | | | | |

[1]By difference.
[2]Runaway exotherm did not permit steady state operation.
[3]MAcr = methacrolein
MAA = methacrylic acid
HAc = acetic acid
[4]$C_4H_8$ = isobutylene

EXAMPLE 7

A catalyst of the formula $$Sn_{0.05}Sb_{0.07}Te_{0.75}As_{0.12}/Fe_{8.35}Mo_{12.0}P_{3.03}Sb_{0.19}Th_{0.05}O_x$$

is prepared as follows:

Perlite (95 g.) is slurried with 90.8 g. phosphomolybdic acid, 154 g. ferric nitrate, 1.0 g. thorium nitrate, 10.4 g. 85 percent phosphoric acid, 60 ml. 70 percent nitric acid and 810 ml. deionized water. The slurry is agitated at 59° to 63° C. while 390 g. of a 14 percent ammonia solution was added, dropwise, over a 45 minute period. Agitation is continued while a mixture of promoters comprising 2.0 g. molybdenum telluride, 3.1 g. antimony telluride, 0.5 g. tin antimonide, 1.4 g. arsenic telluride, 26.0 g. perlite and 12.6 g. molybdenum trioxide is added. The slurry is agitated vigorously while enough water is stripped to yield a paste amenable to pelletization. After pelletization, the 3/16"×3/16" segments are dried, tumbled with 0.2 g. 200+ mesh arsenic telluride and then calcined in air, at 481° for 8 hours.

The catalyst is tested for acrolein production in a manner similar to that outlined above, with propylene being substituted for the isobutylene feedstock. Here, using a reactor temperature of 468°, 49 percent of the propylene is consumed with 32 percent of that fed going to acrolein and 4.7 percent to acrylic acid. Respective conversions to acetic acid, acetaldehyde, formaldehyde and waste gas are 0.1, 0.0, 1.8, and 10.2 percent.

EXAMPLE 8

The following comprises a comparison of the perlite supported catalyst with unsupported iron-molybdate. This work is to demonstrate that the present invention is superior to iron molybdate, a catalyst of the prior art, which bears a superficial resemblance to the active ingredient of the present invention.

This material is prepared by stirring 1131 g. ferrous sulfate ($FeSO_4 \cdot 7H_2O$) and 708 g. ammonium heptamolybdate, $(NH_4)_6Mo_7O_{24} \cdot 4H_2O$, in 2400 ml. deionized water at 65° to 70°. A solution, prepared by mixing 320 ml. deionized water and 320 ml. 29 percent ammonia, is then added dropwise over a 35 minute period. The olive green precipitate is filtered, washed 5 times with 5 2 l. portions of deionized water, and allowed to stand for 48 hours under 2 l. deionized water. The filter cake is dried and calcined in air at 608° to 643° for 8 hours. Oxidation tests are made with both propylene and isobutylene feedstocks, using methods outlined for the previous catalysts. In Tables II-A and II-B, data are presented for both the prior art composition and the present invention. The superiority of the latter is obvious. Synthesis of the "present invention catalyst" shown here is described in Example 7.

Table II-A

| Comparison of the Perlite Supported Catalyst with Unsupported Iron Molybdate | | | | | | |
|---|---|---|---|---|---|---|
| Propylene Oxidation | | | | | | |
| | Reactor Temp. | Conv. of | Percent Conversion to | | | |
| Catalyst | (° C.) | $C_3H_6(\%)$ | Acrolein | AA | HAc | Waste Gas |
| Present Invention | 422 | 22 | 16.6 | 1.5 | 0.2 | 3.4 |
| | 468 | 49 | 32.0 | 4.7 | 0.1 | 10.2 |
| Prior Art | 438 | 15 | 4.4 | 0.0 | 0.1 | 9.7 |
| | 470 | 14 | 0.0 | 0.0 | 0.0 | 16.1 |

[1]AA = acrylic acid

Table II-B

| Comparison of the Perlite Supported Catalyst with Unsupported Iron Molybdate | | | | | | |
|---|---|---|---|---|---|---|
| Isobutylene Oxidation | | | | | | |
| | Reactor Temp. | Conv. of | Percent Conversion of | | | |
| Catalyst | (° C.) | $C_4H_8(\%)$ | MAcr | MAA | HAc | Water Gas |
| Present Invention | 374.0 | 59. | 38.1 | 1.0 | 3.3 | 12.6 |
| Prior Art | 370.0 | 22. | 4.7 | 0.0 | 1.4 | 15.2 |

In all of the foregoing examples where perlite is used, before the catalyst is made the perlite has a total surface area of less than 15 m.²/g., a total porosity of at least 2.5 cc./g., at least 40 percent of the pores being greater than 100,000 A in diameter, and no more than 25 percent of the pores being less than 10,000 A in diameter.

EXAMPLE 9

When Example 1 is repeated but in which the feed is isobutylene:ammonia:air:steam in the mole ratios 101.2:15:7, methyacrylonitrile is obtained in the product stream.

EXAMPLE 10

When Example 6 is repeated with a feedstock of propylene:ammonia:air:steam in a molar ratio of 1:1:5:7, acrylonitrile is obtained in the product.

It is to be understood that in the foregoing wherever "hollow bubbles," "glassy bubbles," "microballoons," and "hollow spheres," are mentioned in connection with expanded perlite prior to its being crushed, applicants intend to include expanded particles having a foam-like structure wherein the tiny particles have a number of individual cells connected to one another. Such multicellular particles are illustrated in the article "Petrographic Techniques in Perlite Evaluation," Trans. AIME, Volume 226, pages 332–336, by F. L. Kadey, Jr. (1963).

It is also to be understood that the catalyst per se is useful for other processes than for the preparation of saturated aldehydes, nitriles, and acids by the vapor phase oxidation of the corresponding mono-olefin. In this connection, the catalysts are useful for converting n-butene-1 to butadiene-1,3. One way in which this may be done is by simultaneously producing butadiene, methacrolein, and, usually, some methacrylic acid, utilizing a four carbon atom cut from cracking hydrocarbons such as naphtha reforming, thermal gas cracking, and catalytic gas oil cracking. This four carbon fraction is difficult to separate into n-butene, isobutene (isobutylene), and the saturated isobutane and n-butane. This separation makes the unsaturated products quite expensive to obtain. Commonly, the ratio of isobutene to n-butene is in the range of 1:1 to 1:4, although other ranges of course are useful, as are mixtures of four carbon atom hydrocarbons other than those from cracking the named hydrocarbon. The reaction conditions are suitably the same as those for producing methacrolein from isobutylene. This simultaneous preparation of butadiene-1,3 and methacrolein is discussed in greater detail in Netherlands Patent Application 69/12457, published on Feb. 17, 1970 and assigned to Japanese Geon Co. Limited, but with a different catalyst.

I claim:

1. An oxidation catalyst system, having a metal oxide catalyst on a support, in calcined form, wherein the catalyst has the formula, on an atomic basis, of $Sb_{0.1-1}Sn_{0-.1}Te_{.001-1}As_{0-1}A_{0-1}Y_{12}X_{2-12}Th_{.01-1}U_{0-2}Si_{0-50}P_{0-5}O_x$, werein A is Bi, Cd, or both, X is Fe, Co, or both, Y is Mo, W, or both, the symbol "Ox" indicating that oxygen is combined with elements recited in the formula.

2. The catalyst of claim 1 in which A is Bi, present in a finite amount.

3. The catalyst of claim 1 in which A is Cd, present in a finite amount.

4. The catalyst of claim 1 in which X comprises Fe.

5. The catalyst of claim 1 in which X comprises Co.

6. The catalyst of claim 4 in which Y is Mo, and A is Bi, present in a finite amount.

7. The catalyst of claim 5 in which Y is Mo, and A is Bi, present in a finite amount.

8. The catalyst of claim 4 in which Y is Mo, and A is Cd present in a finite amount.

9. The catalyst of claim 5 in which Y is Mo, and A is Cd present in a finite amount.

* * * * *